United States Patent [19]

Carney

[11] Patent Number: 4,898,932
[45] Date of Patent: Feb. 6, 1990

[54] MONOCLONAL ANTIBODIES REACTIVE WITH ACTIVATED AND ONCOGENIC RAS P21 PROTEINS

[75] Inventor: Walter P. Carney, Brighton, Mass.

[73] Assignee: E. I. Du Pont de Nemours and Company, Wilmington, Del.

[21] Appl. No.: 111,315

[22] Filed: Oct. 22, 1987

Related U.S. Application Data

[63] Continuation-in-part of Ser. No. 913,905, Oct. 1, 1986, abandoned, and a continuation-in-part of Ser. No. 696,197, Jan. 19, 1985, abandoned.

[51] Int. Cl.$^4$ .......................... C07K 15/00; C12N 5/00
[52] U.S. Cl. .................................... 530/387; 530/388; 530/808; 530/809; 424/85.8; 435/70.21; 435/172.2; 435/240.1; 435/240.26; 435/240.27; 935/89; 935/95; 935/102; 935/103; 935/106; 935/108; 436/548
[58] Field of Search ................... 530/387.88, 808–809; 424/85.8; 435/68, 172.2, 240.1, 240.26, 240.27; 935/89, 95, 102–103, 106, 108

[56] References Cited

U.S. PATENT DOCUMENTS

| | | | |
|---|---|---|---|
| 4,568,640 | 2/1986 | Rubin | 935/20 |
| 4,699,877 | 10/1987 | Cline et al. | 435/7 |
| 4,725,550 | 2/1988 | Perucho et al. | 435/68 |
| 4,762,706 | 8/1988 | McCormick et al. | 424/85 |
| 4,786,718 | 11/1988 | Weinberg et al. | 530/387 |
| 4,820,631 | 4/1989 | Lacal et al. | |

FOREIGN PATENT DOCUMENTS

| | | |
|---|---|---|
| 0108564 | 5/1984 | European Pat. Off. |
| 0175360 | 3/1986 | European Pat. Off. |
| 0177814 | 4/1986 | European Pat. Off. |
| 190033 | 8/1986 | European Pat. Off. |
| 0259197 | 12/1985 | Japan |
| 8403087 | 8/1984 | PCT Int'l Appl. |
| WO85/00807 | 2/1985 | PCT Int'l Appl. |

OTHER PUBLICATIONS

Sevier et al., Clin. Chem. 27(11) 1981, pp. 1797–1806.
Zaparowsky et al., Cell 34, 1983, pp. 581–586.
Ohuchi et al., Cancer Res. pp. 2511–2519, vol. 46 (May 1986).
McCormick et al., (Wong), Cancer Res. pp. 6029–6033, vol. 46 (Dec. 1986).
Proc. Natl. Acad. Sci. U.S.A., pp. 7485–7489, vol. 83 (Oct. 1986).
Cetus Product Inserts (1985)-attached to Comp. Results Decl.
Zarbl et al., "Direct Mutagenesis of Ha-ras-1 Oncogenes by N-nitroso-N-methylurea During Initiation of Mammary Carcinogenesis in Rats", pp. 382–385, vol. 315, May 30, 1985, Nature.
Santos et al., "Malignant Activation of K-ras Oncogene in Lung Cancinoma but Not in Normal Tissue of Same Patient", pp. 661–664, Feb. 17, 1984, vol. 223, Science.
Furth et al., "Monoclonal Antibodies to the p21 Products of the Transforming Gene of Harvey Murine Sarcoma Virus and of the Cellular ras Gene Family", pp. 294–304, Jul. 1982, vol. 43, No. 1, J. of Virology.
Gallick et al., "Expression of p21$^{ras}$ in Fresh Primary and Metastatic Human Colorectal Tumors", pp. 1795–1799, Mar. 1985, vol. 82, PNAS.
Kuzrock et al., "Differential Expression of p21$^{ras}$ Gene Products Among Histological Subtypes of Fresh Primary Human Lung Tumors", pp. 1530–1534, Mar. 1986, vol. 46, Cancer Research.
Hand et al., "Monoclonal Antibodies of Predefined Specificity Detect Activated ras Gene Expression in Human Mammary and Colon Carcinomas", pp. 5227–5231, Aug. 1984, vol. 81, PNAS.
Thor et al., "Monoclonal Antibodies Define Differential ras Gene Expression in Malignant and Benign Colonic Diseases", pp. 562–565, Oct. 11, 1984, vol. 311, Nature.
Taparowsky et al., Banbury Report, 14:123–133 (1983) cited in Chem. Abstracts, CA 100(1):1425n.
Shimizu et al., Nature, 304(5926), 497–500 (1983), cited in Chem. Abstracts, CA 99(19):153093b.
Fasano et al., J. Mol. Appl. Genet., 2(2):173–180 (1983), cited in Chem. Abstracts, CA 99(19):153080v.
Andreeff et al., Blood, pp. 676–681, vol. 67, No. 3, Mar. 1986.
Bos et al., Nature, pp. 726–730, vol. 315, Jun. 27, 1985.
Carney et al., UCLA Symposia, Jan. 20–Feb. 15, 1986, Colorado.
Carney et al., Fifth Annual Congress for Hybridoma Research, Jan. 26–29, 1986, Baltimore, Md.
Carney et al., J. Cell. Bio., pp. 207–214, vol. 32, 1986.
Carney et al., Monoclonal Antibodies & Cancer Therapy, pp. 565–572 (1985).
Carney et al., Monoclonal Antibody Raised Against Synthetic Peptide Shows Immunoreactivity with Human Carcinoma Cells, 69th Ann. Mtg. of FASEB, Apr. 1985.
Carney et al, Apr. 1986 Mtg. of Federation of American Societies for Experimental Biology (FASEB).
Carney et al., UCLA Symp. Mol. Cell Biol., New Ser., pp. 565–572, vol. 27 (1985), CA vol. 104 (1986), No. 166570B.

(List continued on next page.)

Primary Examiner—Garnette D. Draper

[57] ABSTRACT

Monoclonal antibodies reactive with oncogenic and activated ras p21 proteins containing glutamic acid, arginine or valine at position 12 and unreactive with normal ras p21 proteins containing glycine at position 12. The antibodies are secreted by hybridomas obtained by immunizing mice with synthetic dodecapeptides corresponding in amino acid sequence to positions 5–16 of normal ras p21 proteins, except having glutamic acid, arginine or valine in place of glycine at position 12. The antibodies and Fab fragments thereof are useful for diagnosis, staging and classification of malignant and premalignant lesions.

13 Claims, No Drawings

OTHER PUBLICATIONS

Caruso et al., Int. J. Cancer, pp. 587–595, vol. 38 (1986).
Chang et al., Nature, pp. 479–483, vol. 297 (Jun. 10, 1982).
Clark et al., PNAS (U.S.A.), pp. 5280–5284, vol. 82, No. 16, (Aug. 1985).
Cooper et al., Biochimica et Biophysica Acta, pp. 9–20, vol. 738 (1984).
Der et al., Cell, pp. 167–176, vol. 44, Jan. 17, 1986.
Feramisco et al., Nature (England), 314(6012): 639–642, Apr. 18–24, 1985.
Finkel et al., Cell, pp. 151–158, vol. 37, (May 1984).
Gambke et al., Nature, pp. 476–478, vol. 307 (Feb. 2, 1984).
Ghosh et al., J. Clin. Pathol. (England) 39(4):428–434 (Apr. 1986).
Gibbs et al., PNAS (U.S.A.), pp. 5704–5708, vol. 81 (Sep. 1984).
Hamer et al., The Amer. Commercial & Industrial Conference & Expo. in Biotechnology, Apr. 27–May 1, 1986, Boston, Mass.
Herlyn et al., J. Clin. Immunology, pp. 135–140, vol. 2, No. 2, 1982.
Lacol et al., Molecular & Cellular Biology, vol. 6, No. 4, pp. 1002–1009 (Apr. 1986).
Lefebvre et al., Lab. Invest. 54:35a, Jan. 1986.
Manne et al., PNAS (U.S.A.), pp. 376–380, vol. 82, Jan. 1985.
McGrath et al., Nature, vol. 310 23, pp. 644–649, Aug. 1984.
Metzgar et al., Cancer Research, pp. 601–608, vol. 42, Feb. 1982.
Niman et al., Clin Lab. Med. (U.S.) 6(1):181–196, Mar. 1986.
Niman et al., Proc. Natl. Acad. Sci. U.S.A. vol. 82, pp. 7924–7928, Dec. 1985.
Papageorge et al., J. Virol., pp. 509–519, vol. 44, No. 2, Nov. 1982.
Parada et al., Nature, pp. 474–476, vol. 297, Jun. 10, 1982.
Poe et al., J. Biol. Chem., pp. 3906–3909, vol. 260, No. 7, Apr. 10, 1985.
Reddy et al., Nature, pp. 149–152, vol. 300, Nov. 11, 1982.
Robinson et al., Br. J. Cancer, pp. 877–883, vol. 54 (1986).
Santos et al., Science, pp. 661–664, vol. 223, Feb. 17, 1984.
Santos et al., Nature, pp. 343–344, vol. 298, Jul. 22, 1982.
Schlom, cited in The 5th Annual Congress for Hybridoma Research, pp. 165–166, Jan. 26–29, 1986, Baltimore, Md.
Scolnick et al., PNAS (U.S.A.), pp. 5355–5359, vol. 76, Oct. 1979.
Shilo et al., Nature, pp. 607–609, vol. 289, Feb. 12, 1981.
Srivastava et al., Mol. Cell. Biol., pp. 3316–3319, vol. 5, No. 22, Nov. 1985.
Sweet et al., Nature, pp. 273–275, vol. 311, Sep. 1984.
Tabin et al., Nature, pp. 143–149, vol. 300, Nov. 11, 1982.
Tahara et al., Jpn. J. Cancer Res. (Gann), pp. 517–522 (1986).
Tanaka et al., Cancer Research, pp. 1465–1470, vol. 46, Mar. 1986.
Tanaka et al., PNAS (U.S.A.), pp. 3400–3404, vol. 82, May 1985.
Wolfe et al., Lab. Invest. 52:77a (1985).
Yuasa et al., Nature, pp. 775–779, vol. 303, Jun. 30, 1983.

MONOCLONAL ANTIBODIES REACTIVE WITH ACTIVATED AND ONCOGENIC RAS P21 PROTEINS

CROSS REFERENCE TO RELATED APPLICATIONS

This application is a continuation-in-part of U.S. Ser. No. 913,905 which was filed on Oct. 1, 1986 now abandoned and U.S. Ser. No. 696,197 which was filed on Jan. 19, 1985 now abandoned.

FIELD OF INVENTION

This invention concerns murine monoclonal antibodies that are immunoreactive with antigens designated activated ras p21s which are common to a variety of malignant cells, both solid tumors and hematopoietic neoplasms. Also of concern are the hybridoma cell lines that secrete the antibodies and the processes that employ the antibodies or antibody fragments of the invention for diagnosis, staging and classification of malignant and premalignant lesions.

BACKGROUND OF THE INVENTION

The immune response to entry of a foreign substance into the body consists of secretion by plasma cells of "antibodies" which are immunoglobulin (Ig) molecules with combining sites that recognize particular determinants on the surface of the foreign substance, or antigen, and bind specifically to them. Immunoglobulin is the generic name of various isotypes of antibodies that include IgG, IgM, IgA, IgE, and IgD. The various species of Ig have similarities and differences. For example, all immunoglobulin molecules have a constant portion, i.e., highly conserved (constant) amino acid sequence, within a particular Ig subclass (e.g., IgG$_1$). This constant region is responsible for various biological effector functions (e.g., complement activation). The portion of the immunoglobulin molecule responsible for immunological specificity (i.e., specific antigen binding) is called the variable region. It is made up of the variable regions of the Ig heavy and light chains. These variable regions differ in amino acid sequence according to the antigenic determinant which the Ig recognizes. Usually, the antibody (Ab) response to an antigen (Ag) is heterogeneous. Upon injection of a body with an immunogen, the body manufactures large numbers of antibodies directed against various determinant sites on the antigen. It is difficult to separate antibodies from conventional antisera containing mixtures of antibodies. It has, therefore, long been a goal to design a continuous source of defined antibodies that recognize and combine with specific antigen determinants.

Hybridoma technology concerns the fusion of myeloma cells with lymphocytes from animals which have been immunized with a particular antigen. The resulting hybridoma cell manufactures monoclonal antibodies that are specific against a single antigenic determinant. Monoclonal antibodies are beginning to replace conventional antisera in standard diagnostic kits for such procedures as the radioimmunoassay. Significant work is also being done to adapt hybridoma technology for therapeutic purposes.

Some properties that flow from an ideal hybridoma cell line are (1) high cloning efficiency; (2) the ability to grow rapidly in a medium supplemented with serum; (3) no secretion of myeloma immunoglobulin (Ig); (4) stable production of large amounts of Ig after fusion; and (5) ability to grow when reinserted into the originating species.

A typical procedure for making hybridomas is as follows: (a) immunize mice with a certain immunogen; (b) remove the spleens from the immunized mice and make a spleen suspension in an appropriate medium; (c) fuse the suspended spleen cells with mouse myeloma cells; (d) dilute and culture the mixture of unfused spleen cells, unfused myeloma cells and fused cells in a selective medium which will not support growth of the unfused myeloma cells or spleen; (e) evaluate the supernatant in each container containing hybridoma for the presence of antibody to the immunogen; and (f) select and clone hybridomas producing the desired antibodies. Once the desired hybridoma has been selected and cloned, the resultant antibody is produced by in vitro culturing of the desired hybridoma in a suitable medium. As an alternative method, the desired hybridoma can be injected directly into mice to yield concentrated amounts of antibody [Kennett, et al., (1981) Ed., *Monoclonal Antibodies*. Hybridomas: A new dimension in biological analyses, Plenum Press, New York].

Hybridomas produced by fusion of murine spleen cells and murine myeloma cells have been described in the literature by Kohler et al., in Eur. J. Immunol. 6, 511–519 (1976); by Milstein et al. in *Nature*, 266, 550 (1977); and by Walsh, *Nature*, 266, 495 (1977).

The technique is also set out in some detail by Herzenberg and Milstein, in *Handbook on Experimental Immunology*, Ed. Weir (Blackwell Scientific, London), 1979, pages 25.1 to 25.7 as well as in Kennett et al., supra.

Patents relating to monoclonal antibodies against human tumors produced by hybridoma technology include U.S. Pat. Nos. 4,172,124 and 4,196,265. Representative of the art concerning monoclonal antibodies that have specificity for antigens on carcinoma cells are U.S. Pat. No. 4,350,683.

Relative to the parent myeloma cell line employed herein for the fusion event, see Kearney et al, *Immunol.*, 123, 1548–1550 (1978).

DNA mediated transfection experiments using NIH3T3 cells as recipients have led to the identification of human transforming genes from a wide variety of tumor types including established cell lines and primary tumor tissues from cancer patients. To date, approximately 20% of all tumor cells tested have been found to contain transforming genes, termed activated ras genes. The ras genes present in mammalian cells have been demonstrated to be homologous to murine sarcoma viral oncogenes. [Weinberg et al., U.S. Pat. No. 4,535,058; Harvey (1964), *Nature*, 104: 1104; Kirsten et al. (1967), J.N.C.I., 39: 311]. Thus, genetic sequences homologous to the ras retroviral oncogenes have been found in neoplastic cells as diverse as carcinomas, sarcomas, neuroblastomas and hematopoietic malignancies [reviewed in Cooper, et al. (1983), *Biochem. Biophys. Acta. Rev.* 738: 9].

Ras genes are found in all nucleated mammalian cells and encode 21,000 molecular weight intracellular membrane proteins designated p21. Viral and cellular ras genes encode membrane bound proteins [Willingham, et al. (1980), *Cell*, 19: 1005] which bind guanine nucleotides [Scolnick, et al. (1979), PNAS (USA), 76: 5355; Papageorge, et al. (1982), *J. Virol.*, 44: 509; and Finkel, et al. (1984), *Cell*, 37: 151] and possess intrinsic GTPase activity [McGrath, et al. (1984), *Nature*, 310: 644; Sweet et al. (1984), *Nature* 311: 273; Gibbs et al. (1984), PNAS (USA), 81: 5704; and Manne et al. (1985) PNAS, 82: 376]. Transfection experiments using NIH3T3 cells as recipients of human tumor DNA have led to the identification of a family of activated human transforming genes homologous to the ras genes of the Harvey (ras$^H$) and Kirsten (ras$^K$) sarcoma viruses. A third member of the ras family designated ras$^N$ has been identified but has not been found to have a retroviral counterpart. Activated ras genes are structurally distinct from their normal homologs, having amino acid substitutions in the protein at positions 12, 13 or 61 [Tabin, et al (1982), *Nature*, 300: 143; Reddy, et al. (1982), *Nature*, 300: 149; Bos, et al. (1985), *Nature*, 315: 716; and Yuasa et al (1983), *Nature*, 303: 775]. The p21 found in normal cells has the following primary amino acid structure for residues 5 through 16: $^5$Lysine-leucine-valine-valine-valine-glycine-alanine-glycine-glycine-valine-glycine-lysine$^{16}$. In contrast to normal cells, neoplastic cells have been shown to have amino acid substitutions such as glutamic acid or arginine at position 12 with amino acid residues 5, 6, 7, 8, 9, 10, 11, 13, 14, 15 and 16 being identical to those in normal p21 proteins. [Zarbl et al., *Nature* (London) 315: 382 (1985); Santos et al., *Science*, 223: 661 (1984).]

Similarly, neoplastic cells such as the T24 bladder carcinoma have been shown to have an amino acid substitution such as valine at position 12 with amino acid residues 5, 6, 7, 8, 9, 10, 11, 13, 14, 15 and 16 being identical to those found in P21 molecules in untransformed cells.

Previous reports [Furth et al. (1982), *J. Virol.*, 43: 294] have described several rat monoclonal antibodies reactive with normal and activated (mutated) ras p21 proteins in yeast and mammalian cells. One such broadly reactive monoclonal antibody Y13-259 (Id.) has been utilized in Western blot studies to describe elevated levels of ras p21 in human colon and lung carcinoma cells. However, due to the broad cross reactivity of Y13-259, it could not be determined whether the elevated ras in these carcinoma cells was due to activated or normal ras expression [Gallick et al. (1985), PNAS (USA) 82: 1795; Kurzrock et al. (1986), *Cancer Res.*, 46: 1530]. Similarly, monoclonal antibodies raised against ras related synthetic peptides and designated RAP have been shown to be broadly reactive with breast and colon carcinomas; however, this antibody has also been shown to react with normal and mutated ras proteins [Horan et al. (1984), PNAS, 82: 5277; Thor, et al. (1984), *Nature*, 311: 562].

The subject of this invention is the induction, production and characterization of monoclonal antibodies that react with activated ras proteins containing amino acid mutations at position 12 and that do not react with proteins containing the normal amino acid glycine at position 12. Antibodies E184 and E170 react with activated (oncogenic) ras proteins containing glutamic acid at position 12 instead of glycine, R256 reacts with activated (oncogenic) ras proteins containing arginine at position 12 and DWP reacts with activated (oncogenic) ras proteins containing valine at position 12. Described in this invention are valuable diagnostic tools for the detection staging and classification of primary and metastatic neoplastic cells.

STATEMENT OF DEPOSIT

1. The hybridoma cell lines which were found to secrete a monoclonal antibody reactive with activated ras proteins containing glutamic acid at position 12 and the subject of this invention were deposited in the American Type Tissue Culture Collection (ATCC) under the Budapest Treaty. Hybridoma E184 was designated HB9194 and E170 was designated HB9195.

2. The hybridoma cell line which was found to secrete a monoclonal antibody reactive with an activated ras protein containing arginine at position 12 and also the subject of this invention was deposited in the ATCC under the Budapest Treaty with the accession number HB9196 and is hereafter referred to as R256.

3. The hybridoma cell line which was found to secrete a monoclonal antibody reactive with an activated ras protein containing valine at position 12 and also the subject of this invention was deposited in the ATCC under the Budapest Treaty with the accession number HB8698 and is hereafter referred to as DWP.

SUMMARY OF THE INVENTION

Balb/c×C57B1/6 mice were immunized on several occasions with synthetic dodecapeptides coupled to carrier proteins. In the case of antibodies E170 and E184 mice were immunized with peptides containing the following primary amino acid structure: $^5$Lysine-leucine-valine-valine-valine-glycine-alanine-glutamic acid-glycine-valine-glycine-lysine$^{16}$. In the case of monoclonal antibody R256 mice were immunized with the following peptide: $^5$Lysine-leucine-valine-valine-valine-glycine-alanine-arginine-glycine-valine-glycine-lysine$^{16}$. In the case of monoclonal antibody DWP mice were immunized with peptides containing the following primary amino acid structure: $^5$Lysine-leucine-valine-valine-valine-glycine-alanine-valine-glycine-valine-glycine-lysine$^{16}$.

Spleen cells from immune mice were fused with Sp/2-0 mouse myeloma cells and two weeks later culture supernatants were screened by enzyme-linked immunosorbent assay (ELISA) for reactivity with the immunogen. Hybridomas secreting antibodies E184 or E170 were selected because of their reactivity on the peptide-immunogen containing glutamic acid at position 12 and because of their lack of reactivity with peptides containing glycine at position 12.

Monoclonal antibodies E170 and E184 show specificity for dodecapeptides containing glutamic acid at position 12 but do not react with dodecapeptides containing glycine, aspartic acid, serine, arginine, cysteine, alanine or valine at position 12.

Further analysis of NIH cells transformed with various activated ras proteins indicated that E170 and E184 specifically react by Western blot procedures with activated ras proteins with glutamic acid at position 12. Antibodies E170 and E184 did not react however with normal cellular ras proteins (glycine at position 12) or activated cellular ras proteins containing amino acid substitutions valine, aspartic acid, arginine, cysteine or serine at position 12.

Hybridoma R256 was selected because of its reactivity on the immunizing peptide containing arginine at position 12 and because of its lack of reactivity with peptides containing glycine at position 12.

Monoclonal antibody R256 specifically reacted with dodecapeptides containing arginine at position 12 but did not react with dodecapeptides containing glycine, glutamic acid, aspartic acid, serine, cysteine, valine or alanine at position 12.

Further analysis of NIH cells transformed with various activated ras proteins indicated that R256 specifically reacted by Western blot procedures with activated ras proteins with arginine at position 12. Antibody R256 did not react however with normal cellular ras proteins (glycine at position 12) or activated cellular ras proteins containing amino acid substitutions valine, glutamic acid, aspartic acid, cysteine or serine at position 12.

Hybridoma DWP was selected because of its reactivity on the immunizing peptide containing valine at position 12 and because of its lack of reactivity with peptides containing glycine at position 12.

Monoclonal antibody DWP specifically reacted with dodecapeptides containing valine or cysteine at position 12 but did not react with dodecapeptides containing glycine, glutamic acid, aspartic acid, serine, arginine, or alanine at position 12.

Further analysis of NIH cells transformed with various activated ras proteins indicated that DWP specifically reacted by Western blot procedures with activated ras proteins with valine at position 12. Antibody DWP did not react however with normal cellular ras proteins (glycine at position 12) or activated cellular ras proteins containing amino acid substitutions arginine, cysteine, glutamic acid, aspartic acid, or serine at position 12. The lack of DWP reactivity with cys-containing p21s in Western analysis suggests that the cross-reactivity observed with peptides containing cys at position 12 by ELISA was too weak a reaction to detect cellular p21 by the blot. Thus, by the Western blot procedure, DWP only reacted with ras proteins containing val-12 and not normal p21s or p21s activated by other substitutions.

Antibody E170 is an $IgG_3$ kappa antibody. E184 and R256 are $IgG_1$ kappa antibodies. Antibody DWP was found to be an $IgG2b$ kappa molecule by using rabbit antibodies against various classes of mouse immunoglobulins.

DETAILED DESCRIPTION OF THE INVENTION

Immunization

To produce monoclonal antibody E170 and E184 Balb/c×C57B1/6 mice were immunized intraperitoneally (i.p.) with 500 micrograms (μg) of a dodecapeptide conjugated to carrier protein (keyhole limpet hemocyanin). Peptides were coupled to the carrier proteins in all instances described herein using 1-ethyl-3-(3-dimethylamino-propyl) carbodiimide hydrochloride as described in Goodfriend et al., *Science* (1964), 144: 1344. The primary amino acid structure of the immunizing peptide was $^5$lysine-leucine-valine-valine-valine-glycine-alanine-glutamic acid-glycine-valine-glycine-lysine$^{16}$ (hereinafter "peptide 1"). This peptide corresponded to amino acid position 5–16 of an activated ras protein containing glutamic acid at position 12 instead of the normal glycine. The first inoculation of peptide 1 (500 μg) conjugated to carrier protein was given in complete Freunds adjuvant on day 1, and 3 subsequent inoculations of 500 μg of immunogen were given at two-week intervals. Three days before immune spleen cells were used for fusion, mice were given an i.p. boost with 500 μg of the immunogen. Mouse number 2242 was used to generate E170 and mouse number 2244 was used to produce E184.

To produce monoclonal antibody R256, a Balb/c×C57B1/6 mouse was immunized intraperitoneally (i.p.) with 500 μg of a dodecapeptide conjugated to carrier protein keyhole limpet hemocyanin. The primary amino acid structure of the immunizing peptide was $^5$lysine-leucine-valine-valine-valine-glycine-alanine-arginine-glycine-valine-glycine-lysine$^{16}$ (hereinafter "peptide 2"). This peptide corresponded to amino acid position 5–16 of an activated ras protein containing arginine at position 12 instead of the normal glycine. The first inoculation of peptide 2 conjugated to carrier protein was given in complete Freunds adjuvant on day 1, and 2 subsequent inoculations of 500 μg of immunogen were given at two-week intervals. Three days before immune spleen cells were used for fusion, mice were given an i.p. boost with 500 μg of the immunogen. Mouse number 2793 was used to generate R256.

To produce monoclonal antibody DWP, a Balb/c×C57B1/6 mouse designated 1637 was immunized intraperitoneally (I.p.) with 100 μg of bovine thyroglobulin (Btg) conjugated to a dodecapeptide having the following primary amino acid structure: $^5$lysine-leucine-valine-valine-valine-glycine-alanine-valine-glycine-valine-glycine-lysine$^{16}$ (hereinafter "peptide 3"). This peptide corresponding to amino acid position 5–16 of an activated ras protein containing valine at position 12 instead of the normal glycine. The first inoculation of peptide 3 conjugated to carrier protein was given in complete Freunds Adjuvant on day 1 and subsequent inoculations of 100 μg of immunogen were given on days 14, 28, 41. On day 59, three days before fusion, mouse 1637 was given an I.p. boost of 200 μg of immunogen.

Hybridoma Methodology

Three days after an i.p. boost with immunogen (peptide 1 in case of E170 and E184; peptide 2 in case of R256; peptide 3 in case of DWP), the spleen of the appropriate immune mouse was removed and fused with the Sp2/0 cell. More particularly, after sacrifice of the mouse the spleen was removed, cells dispersed into a single cell suspension in serumless DMEM-high glucose medium. Spleen cells were mixed with Sp2/0 cells at a ratio of 4:1. This cell mixture was centrifuged at 1200×g for 10 minutes at room temperature. After removal of the supernatant, the cells were resuspended by gently tapping the tube. The fusion procedure was initiated by adding 1.0 ml of 45% w/v polyethylene glycol 3350 (Baker) at 37° C. over a 30-second period. The cells were mixed occasionally with a pipette tip for 90 seconds and 5 ml of serumless DMEM-high glucose medium was added over a 3 minute period. This was followed by the addition of 14 ml of DMEM-high glucose supplemented with 10% fetal calf serum, L-glutamine, hypoxanthine, aminopterin and thymidine (HAT). The HAT medium was added over a 1-minute period [Kennett et al., supra].

Total volume was adjusted to 50 ml with HAT medium and the cells were centrifuged at 800×g for 7 minutes at room temperature. Supernatants were aspirated and the cell pellet disrupted with 10 ml of HAT medium. 5×10$^5$ Peritoneal cells (Balb/c×C57B1/6) were added. Cells were than pipetted into 96 well microtiter wells at a final concentration of 2×10$^5$ spleen cells per well. Approximately 14 days later, supernatants from wells containing hybridoma colonies were tested by ELISA for the desired reactivity with peptides conjugated to carrier proteins as described below. Hybridomas producing the desired antibodies were cloned by limiting dilution such that 1 cell was plated for every 3 wells as described in Kennett et al., supra.

Once colonies appeared (10–14 days later), the presence of antibody in the culture supernatant was determined by ELISA.

Hybridomas secreting the antibodies of interest were cloned two times and then inoculated into Pristane-primed mice for ascites production. Ascites fluid was then used to prepare purified immunoglobulin as described [Fahey, J., 1967, in *Methods in Immunology and Immunochemistry*, Vol. 1, pp. 307–334]. Purified antibodies were determined by ELISA to be IgG kappa molecules using rabbit antibodies against various classes of mouse immunoglobulins.

Screening Procedures and ELISA Protocol

For screening purposes peptides 1, 2 and 4 were conjugated to carrier protein bovine thyroglobulin [Goodfriend, et al (1964), *Science*, 144: 1344]. For screening purposes peptide 3 was conjugated to carrier protein keyhole limpet hemocyanin (KLH). Peptide 4 consisted of a dodecapeptide representing the normal primary amino acid structure for positions 5–16. Peptide 4 has the following structure: $^5$Lysine-leucine-valine-valine-valine-glycine-alanine-glycine-glycine-valine-glycine-lysine$^{16}$. Prior to screening hybridoma supernatants, 500 nanograms (ngs) of either peptide 1, 2, 3 or 4 conjugated to the appropriate carrier protein was dispensed to 96 well microtiter plates for overnight incubation at 37° C. After incubation, plates were washed and unbound sites were blocked with bovine serum albumin (BSA).

At the time of screening 50 μl of supernatant fluid from hybridoma E170 or E184 was added to wells containing carrier protein bound to either peptide 1 or peptide 4. For screening of R256 wells contained carrier protein bound to either peptide 2 or peptide 4. For screening of DWP wells contained carrier protein bound to either peptide 3 or 4. Supernatants were incubated overnight at 4° C., removed the next day and wells washed with BSA. Each well then received 50 μl of goat anti-mouse IgG antibody conjugated to horseradish peroxidase (GAMHRP) diluted in BSA phosphate buffered saline (PBS).

Wells were incubated for 60 minutes at 37° C. GAMHRP was removed after incubation and wells were washed three times with PBS-BSA mixtures. The presence of bound GAMHRP was determined by adding 50 μl of the substrate o-phenylene diamine (OPD) in phosphate buffer containing 0.15% hydrogen peroxide. HRP in combination with its substrate (OPD) results in a yellow colored product. Development of the yellow product was allowed to occur at room temperature for 15 minutes. The enzymatic reaction was terminated by the addition of 50 μl of 4.5M $H_2SO_4$. Measurement of the resultant reaction product was accomplished by determining optical density (OD) at 488 nm. Presence of yellow color in the wells indicated that the mouse antibody was present in the hybridoma supernatant.

Titration of the DWP Antibody on KLH-Peptide Conjugates

After the DWP hybridoma had been cloned by limiting dilution, it was grown in serumless media for 5 days and the DWP antibody concentrated by ammonium sulfate ($NH_4SO_4$) precipitation.

The concentrated DWP antibody was then evaluated by ELISA for reactivity to KLH conjugated peptide 3, as well as peptides with glycine at position 12 (peptide 4) and cysteine at position 12 (peptide 5). The DWP antibody showed little or no reactivity (as indicated by measuring optical density at 488 nm) on peptide 4 whereas the DWP antibody showed reactivity at several dilutions of peptide 3.

Competition Assays

To evaluate E170, E184, R256 and DWP for specificity on peptides the following assay was performed. E170 and E184 monoclonal antibodies were incubated with peptides (15.6 to 500 ng/well) identical to peptide 4 except that position 12 contained various amino acid substitutions. Substitutions included glutamic acid, aspartic acid, arginine, serine, cysteine, alanine and valine. Peptide-antibody mixtures were then tested for the presence of free antibody by adding the mixtures to plates containing peptide 1 (glutamic acid at position 12), then adding GAMHRP in PBS-BSA followed by OPD. E170 and E184 only bound peptides containing glutamic acid at position 12 demonstrating their specificity. Similar experiments with plates containing peptide 2 demonstrated that R256 was only reactive with peptides containing arginine at position 12. Similar experiments with plates containing peptide 3 demonstrated that DWP was only reactive with peptides containing valine at position 12 and surprisingly is reactive with a peptide not used in the immunization containing cysteine at position 12. These experiments demonstrate that E170 and E184 are specific for peptides containing glutamic acid at ras position 12, R256 specific for peptides containing arginine at ras position 12, and DWP specific for peptides containing valine aline at position 12.

Immunoblot

In order to determine whether E170, E184, R256 and DWP react with intact ras proteins an immunoblot procedure was performed on cells containing the specifically activated ras proteins. In the case of E170 and E184 cell line S-2 was used. This cell line was provided by Dr. M. Barbacid, Frederick Cancer Facility, Frederick, MD. This cell line contains an activated ras protein expressing the glutamic acid mutation at position 12 instead of glycine. Cell line viral-Harvey-ras (V-Ha-ras) (provided by Dr. G. Cooper, Dana Farber Cancer Instituted, Boston, MA) contains an activated ras protein with arginine at position 12 and was used to characterize the R256 antibody. Transformed NIH cells in this study were used to characterize the DWP antibody.

Cell lines S-2 and V-Ha-ras and NIH3T3(T24) were inoculated into nude mice to generate subcutaneous tumors. Tumors were removed from mice two to four weeks later and cell extracts tested for reactivity with E170, E184 and R256. Cell extracts were prepared in Triton X100 lysis buffer and the p21s concentrated from the cell extracts by immunoprecipitation with the broadly reactive anti-ras MOAb, Y13-259 [Further, et al., supra]. For Western blot analysis, immunoprecipitates were collected, washed and boiled in sample buffer containing 2-mercaptoethanol. Immunoprecipitated proteins as well as heavy and light immunoglobulin chains were resolved by SDS-PAGE in 12.5% polyacrylamide and transferred to nitrocellulose membranes. After blocking with PBS containing 5% bovine serum albumin (BSA) membranes were incubated for one hour with 25 μg/ml of Y13-259, E70, E184, R256, MOPC 141 or MOPC 21. Membranes were washed 3 times with PBS-NP-40 (0.05%), incubated with either rabbit anti-rat horseradish peroxidase (HRP)

to detect Y13-259 or goat anti-mouse HRP for 1 hour to detect E170, E184, R256, MOPC 141 or MOPC 21. Membranes were then washed 3 times with PBS-NP-40 and incubated with 4-chloro-1-napthol substrate to complete the reaction.

Immunoblot results demonstrated that E170 and E184 detected only ras proteins containing glutamic acid at position 12. E170 and E184 did not react with normal ras proteins (glycine-12) or other oncogenic ras proteins activated by position 12 substitutions such as valine, cysteine, serine, arginine and aspartic acid. Immunoblot results also demonstrated that R256 detected only ras proteins containing arginine at position 12. R256 did not react with normal ras proteins or other oncogenic ras proteins activated by position 12 substitutions such as valine, cysteine, serine, glutamic acid and aspartic acid. DWP was reactive with p21 of NIH cells transformed by either activated EJ HRAS or SW480 KRAS, both of which encode valine-12. In contrast, DWP was not reactive with normal ras proteins or other oncogenic ras proteins activated by position 12 substitutions such as serine, arginine, aspartic acid and glutamic acid. No reactivity with Cys-containing p21s in immunoblot analysis was detected. This suggests that the cross-reactivity observed with [cys$^{12}$] peptides by ELISA was too weak a reaction to detect cellular p21 by the blot. Thus, by the immunoblot procedure, DWP only reacted with [val$^{12}$]p21 and no normal p21s or p21s activated by other substitutions.

Monoclonals antibodies E170, E184, R256 and DWP specifically react with activated ras proteins in malignant cells and do not react with ras proteins found in normal cells. Therefore, these monoclonal antibodies will be useful in the differentiation of normal and neoplastic cell in various immunological and biochemical assays. Secondly, these antibodies will permit the classification of neoplastic cells into various categories based on the particular ras protein expressed. These antibodies will be useful therefore in the quantitation of activated ras proteins which in turn will be useful in staging tumors based on levels of ras p21 expression. Thus, better diagnosis of malignant cells, the ability to differentiate malignant from premalignant cells and the ability to classfiy malignant cells into various categories due to levels of ras expression will result from the application of monoclonal antibodies E170, E184, R256 and DWP.

Immunohistochemistry by Immunoperoxidase Staining

Six micron tissue sections fixed with formalin and embedded in paraffin were used to evaluate the clinical usefulness of the DWP antibody.

Fixed tissues were deparaffinized in xylene for 30 minutes at 65° C. followed by a 30 minute incubation in xylene at room temperature. Tissues were washed two times in 100% ethanol followed by two washes with 95% alcohol. Tissue sections were thoroughly rinsed in water followed by washing in PBS. Tissues received normal horse serum for a 30 minute incubation to block nonspecific sticking. The monoclonal antibody secreted by hybridoma DWP was applied (2 μg/slide) and incubated overnight at 4° C. After overnight incubation the tissue sections were washed 3 times in PBS and then incubated for 30 minutes with biotinylated horse anti-mouse reagents. Tissue sections were washed with PBS and incubated for 30 minutes with avidin-biotinylated horseradish peroxidase complex. Tissue sections were rinsed in PBS 3 times and reacted with diaminobenzidine and hydrogen peroxide for 5 minutes. The tissue sections were rinsed in PBS, counterstained with hematoxylin for 30 seconds, washed for 30 seconds in alcohol, washed for 30 seconds in ammonium sulfate reagent and dehydrated. Dehydration was carried out by dipping sections in 80% ethanol for 30 seconds, in 95% ethanol for 30 seconds, in 100% ethanol for 30 seconds with two changes in xylene for 10 minutes. Slides were then mounted and examined by microscope to determine the presence of a brownish precipitate which indicates the presence of DWP antibody. The tissue staining as determined by immunoperoxidase reactivity on a variety of normal and neoplastic tissues is summarized in Tables 1 and 2, however the most notable observations are the following:

(1) Positive immunoperoxidase reactivity on 4 out of 8 infiltrating ductal carcinomas of the breast and no reactivity on 1 case of fibrocystic disease.
(2) Positive immunoperoxidase reactivity on 5 out of 6 large cell undifferentiated carcinomas of the lung.
(3) Positive immunoperoxidase reactivity on 2 out 2 oat cell or small cell carcinomas of the lung.
(4) Positive reactivity on primary lesion of oat cell carcinoma as well as positive reactivity of that oat cell carcinoma after its metastasis to the lymph node.
(5) Positive immunoperoxidase reactivity on 7 of 8 colon adenocarcinomas and 4 of 6 villous adenomas of the colon.
(6) Positive immunoperoxidase reactivity on 2 out of 2 endometrioid carcinomas.
(7) Positive immunoperoxidase reactivity on the metastatic carcinoma from the common bile duct.
(8) Negative immunoperoxidase reactivity on apparently normal tissues adjacent to the above (1-7) described carcinomas and no reactivity on normal tissues listed on Table 2.
(9) All carcinoma tissues were negative in control studies whereby the MOPC 141 IgG2b class matched antibody control was substituted for the DWP antibody at the same antibody concentration.
(10) Analysis of cell line PSV-13 (overexpression of ras P21 protein containing the normal amino acid glycine at position 12) by immunoperoxidase staining indicated no staining by the DWP antibody. In contrast, a cell line designated PSV-LM (EJ) containing high overexpression of the mutant ras P21 protein containing valine at position 12 was strongly immunoreactive with the DWP antibody.

TABLE 1

Reactivity Of The DWP Antibody On Neoplastic Tissues By Immunoperoxidase Staining

| Neoplastic Tissue | # Positive/ Total # |
|---|---|
| Breast Carcinoma | |
| Infiltrating Ductal | 4/8 |
| Intraductal Ca. | 0/2 |
| Fibrocystic Disease | 0/1 |
| Lung Carcinoma | |
| Large Cell Undifferentiated | 5/6 |
| Squamous Cell Ca. | 0/2 |
| Adenocarcinomas | 0/1 |
| Oat Cell Carcinoma | 2/2 |
| Oat Cell Metastatic to Lymph Node | 1/1 |
| Colon Carcinoma | |
| Colon Adenocarcinoma | 7/8 |
| Villous Adenoma | 4/6 |
| Ovarian | 0/2 |
| Endometrioid Carcinoma | 2/2 |
| Metastatic Carcinoma from Common Bile | 1/1 |

TABLE 1-continued

Reactivity Of The DWP Antibody On Neoplastic Tissues By Immunoperoxidase Staining

| Neoplastic Tissue | # Positive/ Total # |
|---|---|
| Duct | |

Apparently normal tissue adjacent to tumor cells were unreactive with DWP. The MOPC 141 class-matched IgG2b control was unreactive on tissue sections.

TABLE 2

Formalin-Fixed Paraffin Embedded Normal Tissues And Immunoperoxidase Staining with Antibody DWP

| Tissue Source | # Positive/ Total # |
|---|---|
| Colon | 1/8 |
| Stomach | 2/2 |
| Spleen | 0/10 |
| Lung | 0/10 |
| Liver | 0/10 |
| Heart | 0/10 |

The monoclonal antibody DWP is useful in the diagnosis of primary and metastatic lesions by conventional diagnostic methods. More specifically, the DWP antibody can be used to detect primary carcinomas, including breast, lung and colon cells as well as metastasis to lymph nodes and other organs of the body.

Diagnosis may also be carried out by conventional in vitro diagnostic procedures such as the assay of human blood samples or other bodily fluids. In addition, diagnosis may also be carried out by the evaulation of human tissue sections using this anitbody and immunohistochemical techniques of immunoperoxidase staining; and the detection of micro-lesions containing only a few tumor cells that would not ordinarily be detected by conventional staining techniques is now possible using the monoclonal antibody of this invention.

Immunoreactive Fragments

Immunoglobulins are composed of four chains. The chains of higher molecular weight are designated heavy (H) chains and those of lower molecular weight light (L) chains. Digestion of an immunoglobulin with proteolytic enzymes such as pepsin produces one F(ab')2 molecule and small peptides. The F(ab')2 portion is often referred to as an immunoreactive fragment. An immunoreactive fragment retains the biological activity and specificity of the parent immunoglobulin. Immunoreactive fragments will be used similarly to the parent immunoglobulin molecule. This advantage is they will reduce nonspecific background reactivity. If used in vivo, they will be less immunogenic and quite useful for immunotherapy. [*Handbook of Experimental Immunology*, Vol. 1, 3d Ed., Edited by M. M. Weir, Immunochemistry, Blackwell Scientific Publications.]

This invention includes such immunoreactive fragments of the antibodies of the invention.

I claim:

1. A monoclonal antibody which binds specifically to an epitope of an activated ras protein containing valine at position 12 and does not bind to an epitope of normal nononcogenic ras protein containing glycine at position 12, wherein said epitope of the activated ras protein also is bound by a monoclonal antibody produced by hybridoma cell line having ATCC Accession No. HB 8698.

2. A monoclonal antibody which binds specifically to an epitope of an activated ras protein containing glutamic acid at position 12 and does not bind to an epitope of normal nononcogenic ras protein containing glycine acid at position 12, the epitope of the activated ras protein also is bound by a monoclonal antibody produced by the hybridoma cell lines having ATCC Accession Nos. HB 9194 or HB 9195.

3. A monoclonal antibody which binds specifically to an epitope of an activated ras protein containing arginine at position 12 and does not bind to an epitope of normal nononcogenic ras protein containing glycine at position 12, the epitope of the activated ras protein also is bound by a monoclonal antibody produced by the cell line having ATCC Accession No. 9196.

4. An immunoreactive fragment of the antibody of claim 1.

5. An immunoreactive fragment of the antibody of claim 2.

6. An immunoreactive fragment of the antibody of claim 3.

7. A hybridoma that secretes monoclonal antibody of claim 1.

8. A hybridoma that secretes monoclonal antibody of claim 2.

9. A hybridoma that secretes monoclonal antibody of claim 3.

10. The hybridoma cell line deposited under ATCC Accession No. HB 8698.

11. The hybridoma cell line deposited under ATCC Accession No. HB 9194.

12. The hybridoma cell line deposited under ATCC Accession No. HB 9195.

13. The hybridoma cell line deposited under ATCC Accession No. HB 9196.

* * * * *